United States Patent [19]

Yajima

[11] Patent Number: 4,935,257

[45] Date of Patent: Jun. 19, 1990

[54] METHOD OF PREPARING A STABILIZED VITAMIN POWDER

[75] Inventor: Mizuo Yajima, Tokyo, Japan

[73] Assignee: Asama Chemical Co., Ltd., Tokyo, Japan

[21] Appl. No.: 297,840

[22] Filed: Jan. 13, 1989

[30] Foreign Application Priority Data

Aug. 30, 1988 [JP] Japan ................................ 63-215397
Oct. 4, 1988 [JP] Japan ................................ 63-250310

[51] Int. Cl.$^5$ ............................................. A23L 1/302
[52] U.S. Cl. .................................... 426/555; 426/72; 426/73
[58] Field of Search ................. 426/549, 72, 554, 555, 426/623, 73

[56] References Cited

U.S. PATENT DOCUMENTS

| | | |
|---|---|---|
| 3,959,512 | 5/1976 | D'Alessandro ..................... 426/557 |
| 3,962,416 | 6/1976 | Katzen ................................. 426/73 |
| 4,238,515 | 12/1980 | Shemer ............................... 426/646 |
| 4,305,971 | 12/1981 | Stone .................................. 426/549 |
| 4,483,807 | 11/1984 | Asano et al. ......................... 264/22 |
| 4,517,215 | 5/1985 | Hsu ..................................... 426/451 |
| 4,645,831 | 2/1987 | Lawhon .............................. 426/656 |

FOREIGN PATENT DOCUMENTS 53-130450 11/1978 Japan .................................. 426/549

Primary Examiner—Carolyn Paden
Attorney, Agent, or Firm—Flynn, Thiel, Boutell & Tanis

[57] ABSTRACT

A stabilized vitamin powder comprises one or both of gliadin and glutenin and a vitamin(s).

It is preferable that the powder comprises 100 parts by weight of gliadin and/or glutenin and 1 to 51 parts by weight of vitamins. In the invention, the vitamins may be clathrated and/or coated with gliadin and/or glutenin.

7 Claims, 2 Drawing Sheets

METHOD OF PREPARING A STABILIZED VITAMIN POWDER This invention relates to stabilized vitamin powders and processes for preparing the same.

In recent years, vitamins have been widely used for addition to foods and livestock feeds. Taking into account the ease in handling upon addition to foods or feeds, fat-soluble vitamins are employed by emulsification with an emulsifier or dextrin, followed by drying by a usual drying means for obtaining a powder. However, fat-soluble vitamins are generally liable to be degraded or changed in quality by the influence of heat, light, oxygen and the like. For instance, vitamin A is relatively stable with respect to heat, but is very unstable against oxygen or light, so that it deteriorates in the powdering step and is thus a vitamin which is very difficult to powder. Other fat-soluble vitamins also tend to degrade or change in quality when applied with heat during the course of powdering or when a contact area with air increases after conversion into fine particles by powdering. Thus, it is difficult to obtain a stable powder of the fat-soluble vitamins. On the other hand, water-soluble vitamins are usually in use as crystalline powders and they are in most cases more stable than fat-soluble vitamins in a powdery state. However, the water-soluble vitamins are liable to change in quality when they absorb moisture. Thus, there arises the problem that when these vitamins are added to foods or feeds wherein moisture is absorbed, there is a tendency toward degradation or deterioration caused by the influence of light, oxygen, heat and the like.

To avoid this, stable vitamin powder has been conventionally obtained by a method wherein vitamins are encapsulated in microcapsules in the form of a powder (microcapsule method) or a method wherein vitamins are included with cyclodextrin and powdered (cyclodextrin method). The microcapsule method is complicated in preparation operations with poor productivity and high production costs, coupled with another problem that during storage, the capsules may be broken and that limitation is placed on the type of capsule which is usable in foods or feeds. With the cyclodextrin method, the ratio of materials to be included (vitamins) and cyclodextrin is so small that the resultant product has only a small content of vitamins. In addition, there are further disadvantages that the solubility in water is small and that the included vitamins are released from the cyclodextrin ring by application of heat or by addition to a hydrous material.

For the purpose of enriching feeds for fish, the group of vitamin $B_1$ may sometimes be added. In this case, vitamin $B_1$ is degraded by the action of enzymes in the feed. In order to prevent the degradation with enzymes, there has been adopted a method in which vitamin $B_1$ is covered with a hardened oil or fat. This presents the problem that because of the coverage of the vitamin with a hardened oil or fat, the absorption efficiency of the vitamin in fish lowers.

SUMMARY OF THE INVENTION

Under these circumstances in the art, the present inventors made intensive studies and, as a result, found that when gluten or gliadin or glutenin contained in gluten and vitamins are added to a solvent and agitated, after which the solvent is removed from the mixture and the resultant residue is subjected to powdering, the decomposition or degradation of the vitamins is suppressed and a stable vitamin powder can be obtained.

The invention provides a stabilized vitamin powder which comprises one or both of gliadin and glutenin and a vitamin(s).

It is preferable that the powder comprises 100 parts by weight of gliadin and/or glutenin and 1 to 51 parts by weight of vitamins. In the invention, the vitamins may be clathrated and/or coated with gliadin and/or glutenin.

The invention further provides a process for preparing a stabilized vitamin powder composed of one or both of gliadin and glutenin and vitamins, which comprises the steps of adding gluten to a solvent to dissolve gliadin contained in the gluten into the solvent, adding vitamins to the solution, and then removing out the solvent from the solution to obtain the powder.

The powder of the invention may be prepared by adding glutenin and vitamins to a solvent and then removing out the solvent from the mixture to obtain the powder. It may be prepared by adding gliadin to a solvent, then adding vitamins to the solution, and then removing out the solvent from the mixture to obtain the powder.

The subject matter of the invention resides in:

(1) a stabilized vitamin powder characterized by comprising at least one of gliadin and glutenin and vitamins;

(2) a stabilized vitamin powder according to (1), characterized in that the vitamins are included in the gliadin and/or glutenin;

(3) a stabilized vitamin powder according to (1), characterized in that at least a part of the vitamins are covered with the gliadin and/or glutenin;

(4) a process for preparing a stabilized vitamin powder characterized by comprising adding vitamins to a solvent dissolving gliadin therein under agitation, removing the solvent, and subjecting the resultant residue to powdering;

(5) a process for preparing a stabilized vitamin powder characterized by comprising adding gluten to a solvent under agitation to cause gliadin in the gluten to dissolve in the solvent, adding vitamins to the solution under agitation, removing the solvent, and subjecting the resultant residue to powdering;

(6) a process for preparing a stabilized vitamin powder characterized by comprising adding glutenin and vitamins to a solvent under agitation, removing the solvent, and subjecting the resultant residue to powdering;

(7) a process for preparing a stabilized vitamin powder according to any of (4) to (6) characterized in that the vitamins are dissolved or dispersed in an oil or fat and added to the solvent; and (8) a process for preparing a stabilized vitamin powder according to any of (4) to (7), characterized in that the solvent is a hydrous alcohol having a content of alcohol of 20 to 80% by volume.

The stabilized vitamins of the invention consist of at least one of gliadin and glutenin and vitamins. The gliadin and glutenin are considered to take vitamins in a hydrophobic region of the molecule so as to prevent contact of the vitamins with oxygen, thereby inhibiting decomposition of the vitamins. The vitamins may be included or covered with gliadin and/or gluten, or may be ones which are a mixture of included and covered vitamins. When covered, vitamins may be only partially covered (for example, at reaction sites which undergo the degradation reaction). Alternatively, vitamin particles may be not only covered with a uniform film but also covered on at least part of the surfaces with particles of gliadin and/or glutenin.

The ratio of gliadin and/or glutenin and vitamins in the vitamin powder of the invention is preferably 1 to 51 parts by weight of vitamins per 100 parts by weight of gliadin and/or gluten.

The gliadin is a mixed protein mainly composed of glutamic acid and proline and having an average molecular weight of about 45,000 to 35,000. On the other hand, the glutenin is a protein contained in gluten and having an average molecular weight of several millions. In the practice of the invention, gluten containing gliadin and glutenin can be used as it is. Gluten contains about 40% of each of gliadin and glutenin and about 20% of starch. When water is added to gluten, a very high viscoelasticity is shown, by which gluten is utilized as a thickener, binder or a water retaining agent for addition to foods. It is generally accepted that gliadin contributes to exhibit the viscosity and the elasticity results from glutenin.

The vitamin powder of the invention is obtained by a method wherein gluten and vitamins are added to a solvent and agitated for dissolution or dispersion, after which the solvent is removed and the resultant residue is subjected to powdering, or by a method wherein gliadin is extracted from gluten by the use of a solvent, after which insoluble matters are removed, and vitamins are added to the resultant solution and agitated, followed by removing the solvent from the mixture, and subjecting the resultant residue to powdering, or by a method wherein glutenin and vitamins are added to a solvent and agitated, after which the solvent is removed and the resultant residue is subjected to powdering.

Gluten is soluble in diluted acetic acid, ammonia, a mixture solution of acetic acid and ethanol, and gliadin is soluble in a hydrous alcohol, diluted acids, diluted alkaline solutions and the like. In this connection, however, when gliadin in gluten is allowed to dissolve in a solvent, a hydrous alcohol is favorably used because such an alcohol can suppress swelling of glutenin with water and an increase of viscosity, thus leading to a high working efficiency. On the other hand, where glutenin is used, gliadin is first extracted from gluten with a solvent incapable of dissolving glutenin such as, for example, a hydrous alcohol, after which insoluble matters in the hydrous alcohol (mainly composed of glutenin along with starch) are used by separation. Glutenin is insoluble in a hydrous alcohol, but the hydrous alcohol may be used as a solvent. In this case, glutenin is used by dispersion in the hydrous alcohol.

The gluten may be wet gluten separated from wheat flour or may be activated gluten which has been obtained after drying. In view of workability, the activated gluten in the form of a dried powder is preferred.

The hydrous alcohol may be one which has a content of alcohol of 20 to 80% by volume, preferably from 65 to 75% by volume. The ratio of the hydrous alcohol and gluten is in the range of from 3 to 6 parts by weight, preferably from 4 to 5 parts by weight, of the hydrous alcohol per part by weight of gluten. The alcohol should preferably be monovalent alcohols such as methyl alcohol, ethyl alcohol, isopropyl alcohol and the like. When gluten is added to the hydrous alcohol and agitated, gliadin is extracted from gluten in the hydrous alcohol. The agitation is preferably effected by means of a high speed agitator for a time of not shorter than 30 minutes, by which substantially all gliadin in the gluten can be extracted in the hydrous alcohol.

After addition of vitamins to a solvent dissolving or dispersing gluten or gliadin or to a solvent to which glutenin is added, the mixture is agitated. This agitation is effected for a time of from 10 to 30 minutes or longer, preferably from 15 to 45 minutes by the use of an agitator such as, for example, a high speed homomixer. The amount of the vitamins is preferably from 0.05 to 4 parts by weight per part by weight of gluten and from 0.1 to 4 parts by weight per part by weight of gliadin and/or glutenin.

The vitamins used in the practice of the invention may be either fat-soluble vitamins or water-soluble vitamins. Examples of the fat-soluble vitamins include vitamins A, D and E in a free or ester form. Examples of water-soluble vitamins include a vitamin B group and vitamin C in a free, salt or ester form. These vitamins may be used singly or in combination of two or more.

The vitamins may be added after dissolution or dispersion in animal or plant oils or fats, by which the efficiency of contact between the vitamins and water-soluble enzymes can be lowered considerably, with an increasing effect of preventing degradation with the enzymes. Especially, vitamins $B_1$ should preferably be added to a solvent after dissolution or dispersion in animal or plant oils or fats. Examples of the animal or plant oils or fats include liquid oils such as soybean oil, rape oil and the like and solid fats such as lard, palm and the like. When vitamins are added to feeds, a liquid oil which is well digested and absorbed by fish is preferred.

In the practice of the invention, antioxidants may be added to the solvent, if necessary. The use of an antioxidant can further improve the oxygen resistance. Moreover, synergists such as citric acid, EDTA and the like or other additives such as lecithin may be added, if necessary.

In accordance with the method of the invention, after addition of the vitamins to a solvent and agitation, the solvent is removed and the residue is subjected to powdering. The powdering may be effected by spray drying, drying in vacuum, freeze-drying, drying in drum or other known drying methods.

When a diluted acid is used as a solvent, the pH should preferably be adjusted to 3 to 4. On the contrary, when diluted ammonia is used, the pH should preferably adjusted to 10 to 11. Subsequently, vitamins are added.

The vitamin powder obtained according to the method of the invention is stable when allowed to stand in air or added to hydrous foods and is unlikely to degrade or change in quality by the attack of oxygen, by application of light or heat, by absorption of moisture or by the action of enzymes in foods or feeds. In addition, the powder is advantageous in that when it is added to foods or feeds, the powder has the functions of thickening and binding foods and retaining water in the foods.

As will become apparent from the above, the vitamin powder of the invention rarely degrades or changes in quality by the attack of oxygen, heat, light or enzymes and also by absorption of moisture at the time of addition to foods and has a high content of vitamins with good stability. When the vitamin powder of the invention is added to foods or the like, it exhibits not only the inherent properties, but also can impart other characteristic properties such as thickening, binding, water retention and the like. According to the method of the invention, the vitamin powder of the good properties can be reliably prepared. Gluten is provided relatively inexpensively and gliadin or glutenin is readily available by separation from gluten, so that a highly stabilized vitamin powder can be obtained inexpensively.

Figure 1:
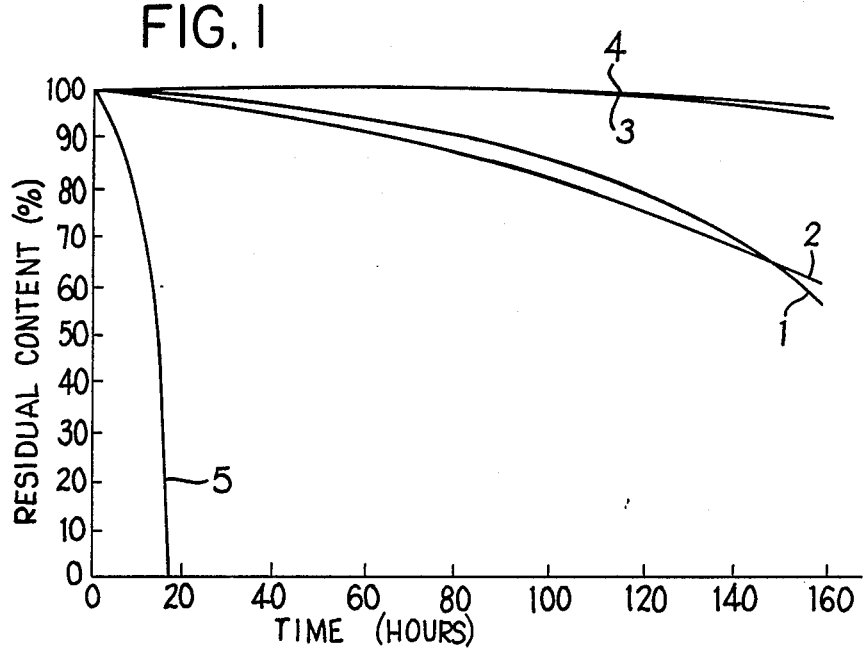
FIG. 1 is a graph showing thermal stability of vitamin A powders of Example 1 and Comparative Example 1.

The present invention is described in more detail by way of examples.

Example 1, Comparative Example 1

1 kg of activated gluten powder was added to 5 liters of hydrous ethanol having a content of the alcohol of 70 vol %, followed by agitation for 30 minutes by the use of an agitator. Subsequently, 45 g of vitamin A palmitate (1,500,000 IU/g) was added to 1 liter of the hydrous ethanol and agitated for 15 minutes, followed by removal of the hydrous ethanol by means of a vacuum dryer and division of the dried matter into fine pieces (vitamin A powder (1)).

On the other hand, the balance of the hydrous alcohol which had been agitated for 30 minutes after addition of the activated gluten was centrifugally separated for 20 minutes at 3000 r.p.m. to remove the resultant precipitate (glutenin, starch and the like). Thereafter, the solution dissolving the gliadin was concentrated to such an extent that the concentration of the gliadin in the hydrous alcohol was 20% (weight/volume percent), after which 45 g of vitamin A palmitate (1,500,000 IU/g) was added to 1 liter of the hydrous alcohol and agitated for 15 minutes by means of a homomixer, followed by drying by the use of a vacuum dryer and powdering to obtain a powder (vitamin A powder (2)).

In the same manner as the method of preparing the vitamin A powder (1) using the hydrous alcohol to which 0.1 wt % of BHT used as an antioxidant was added, vitamin A powder (3) was obtained. Similarly, using the hydrous alcohol to which 0.3 wt % of a rosemary oil (Morukka 10P, available from Asama Kasei K.K.), which is a natural antioxidant, was added, there was obtained vitamin A powder (4).

These vitamin A powders (1) to (4) and vitamin A powder (5) which was obtained by subjecting an emulsion of vitamin A palmitate emulsified by the use of dextrin to dehydration and powdering (Comparative Example) were each heated in an oven at 50° C. in an open system to check the degree of deterioration of the vitamin A with time. The results are shown in FIG. 1. The results revealed that the vitamin A powders obtained according to the method of the invention are significantly more stable than the known vitamin A powder obtained by powdering after the mere emulsification.

Example 2, Comparative Example 2

0.6 g of vitamin $D_3$ crystals (40,000,000 IU/g) dissolved in 45 g of soybean oil was added to 1 liter of each of gliadin-containing hydrous ethanol which was obtained by removing the hydrous ethanol-insoluble matters in the same manner as in Example 1 and having a gliadin concentration of 20% (w/v percent) and a dispersion of hydrous ethanol-insoluble matters (mainly composed of glutenin along with starch and hereinafter referred to simply as crude glutenin) added to hydrous ethanol at a concentration of 20 wt %. Subsequently, the respective mixtures were agitated under the same conditions as in Example 1, from which the solvent was removed by means of a spray dryer to obtain powders (vitamin D powder (1) obtained by the use of the gliadin and vitamin D powder (2) obtained by the use of the crude glutenin).

Figure 2:
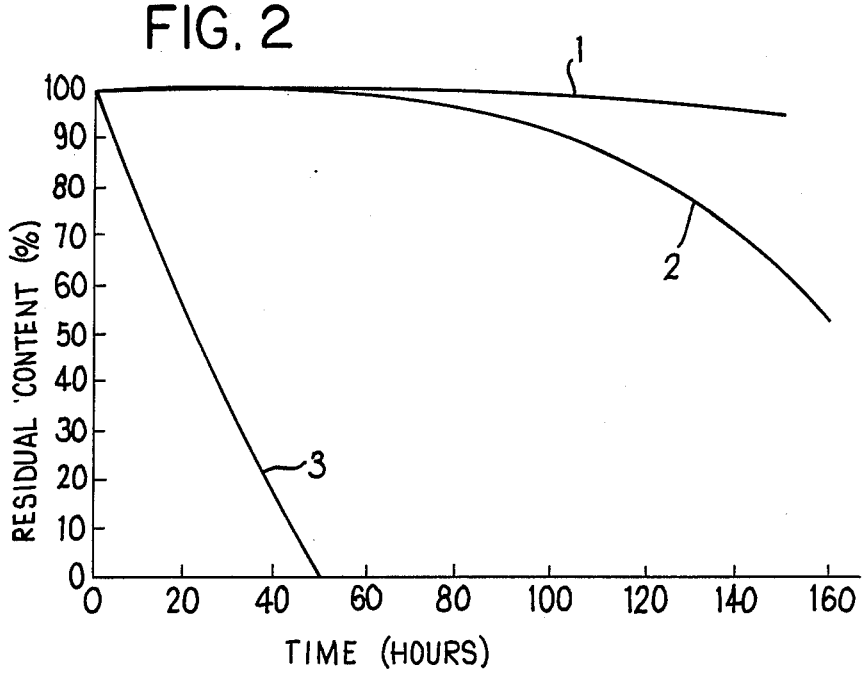
FIG. 2 is a graph showing the thermal stability of vitamin D powders of Example 2 and Comparative Example 2.

The vitamin D powders (1) and (2), and vitamin D powder (3) which was obtained by spray drying an emulsion, with dextrin, of vitamin $D_3$ dissolved in soybean oil wherein the concentration of the vitamin $D_3$ was controlled to have such a concentration as in the above hydrous ethanol (Comparative Example) were each subjected to a heating test under the same conditions as in Example 1. The results are shown in FIG. 2. From the results, it was confirmed that the vitamin $D_3$ powders obtained according to the method of the invention were more stable than the known vitamin $D_3$ powder obtained by powdering after the mere emulsification.

Example 3 and Comparative Example 3

1 kg of activated gluten powder was added to hydrous ethanol having a content of the alcohol of 50 vol % and agitated in the same manner as in Example 1, thereby causing gliadin in the gluten to be dissolved in the ethanol. Thereafter, 20 g of ascorbic acid was added to 1 liter of the hydrous ethanol and agitated, followed by spray drying to obtain vitamin C powder (1). This vitamin C powder (1) and ascorbic acid crystal powder for comparison were, respectively, used to make Vienna sausages (in which when kneading starting materials for the Vienna sausage, the concentration of the ascorbic acid was controlled at 0.1 wt % based on the total weight).

The results of a residue of ascorbic acid in the resultant sausage, yield, color development and elasticity of the product immediately after and 3 weeks after the making are shown in Table 1.

TABLE 1

| | Immediately After Making | 3 weeks After Making |
|---|---|---|
| Example: | | |
| Residual Content of Ascorbic Acid (wt %) | 70 | 30 |
| Yield (%) *1 | 104 | 101 |
| Color Development of Product *2 | good | moderate |
| Elasticity *3 | good | moderate |
| Comparative Example: | | |
| Residual Content of Ascorbic Acid (wt %) | 10 | 0 |
| Yield (wt %) *1 | 100 | 98 |
| Color Development of Product *2 | moderate | poor |

TABLE 1-continued

|  | Immediately After Making | 3 weeks After Making |
|---|---|---|
| Elasticity *3 | moderate | poor |

*1 The yield shows "good" or "poor" of water retention of the product and was compared as an index to the Vienna sausage, as 100%, of the comparative example obtained immediately after the making.
*2 The color development was judged in the following manner by comparison with a standard color of the Vienna sausage of the comparative example obtained immediately after the making.
Good ... a clearer pink color inherent to meat as compared with the standard color
Moderate ... same as the standard color
Poor ... decolored or browned as compared with the standard color.
*3 The elasticity was determined as follows: an elasticity of the product of Comparative Example obtained immediately after the making was judged as moderate, a product with a higher elasticity was judged as good, and a product with a lower elasticity was judged as poor.

As will be apparent from the above results, the vitamin C powders prepared according to the invention allow only a small degree of degradation and a good color development of the resultant products owing to the addition of the vitamin C. Moreover, the water retention and elasticity of the products are also good.

Example 4, Comparative Example 4

10 g of thiamine cetyl sulfate dissolved and dispersed in 190 g of soybean oil was added to hydrous ethanol to which gluten had been added and agitated in the same manner as in Example 1 and agitated, followed by drying in a vacuum dryer to obtain a powder (vitamin $B_1$ powder (1)). A sample wherein 10 g of the powder was added to 1 kg of a thawed sardine mince and a sample wherein 0.1 g of vitamin $B_1$ was added to 1 kg of a similar sardine mince were each stored at 15° C. for 5 hours. Subsequently, both samples were compared with each other with respect to a residual content of the vitamin $B_1$ in the mince. Further, the sardine minces having the respective vitamin $B_1$ prepared in the same manner as described above were thermally treated to deactivate splitting enzymes for vitamin $B_1$ contained in the sardine mince, followed by permitting the mince to be floated in a saline solution of 2° C. which was adjusted at the same concentration as sea water. 5 hours after the floating, the saline solution was filtered and the residue (sardine mince) was subjected to measurement of a residual content of vitamin $B^1$. The results are shown in Table 2.

TABLE 2

|  | Residual Content of Vitamin $B_1$ (wt %) | |
|---|---|---|
|  | after 5 hours at 15° C. | after 5 hours in saline solution |
| Example 4 | 70 | 80 |
| Comp. Ex. 4 | 0 | 5 |

Example 5, Comparative Example 5

1 kg of activated gluten powder was added to 5 liters of hydrous ethanol having a content of the alcohol of 70 vol % and agitated in the same manner as in Example 1. Thereafter, 45 g of vitamin E (total tocopherol of 80 wt %) was added and agitated, followed by spray drying to obtain a powder (vitamin E powder (1)). The total tocopherol content in the vitamin E powder (1) was 16 wt %. The vitamin E powder (1) was added to wheat flour in an amount of 1% and was used to make noodles. On the other hand, an emulsion of vitamin E wherein the total amount of tocopherol was 16 wt % was prepared and was added to wheat flour in an amount of 1 wt % and kneaded to make noodles. These noodles were boiled, after which the residual content of the vitamin E and the quality of the noodles were determined, with the results shown in Table 3.

TABLE 3

|  | Residual Amount of of Vitamin E (wt %) | Quality of Noodle |
|---|---|---|
| Example 5 | 90 | firm and suppressed in dullness when boiled |
| Comp. Ex. 5 | 60 | moderate |

As will be apparent from the above results, the noodles to which the vitamin E powder (1) obtained according to the method of the invention was added are good because of the small loss and degradation of the vitamin E when boiled. After the boiling, the residual content of vitamin E is high with good firmness of the noodles. In addition, the dull expansion of the boiled noodles is prevented.

Example 6, Comparative Example 6

Figure 3:
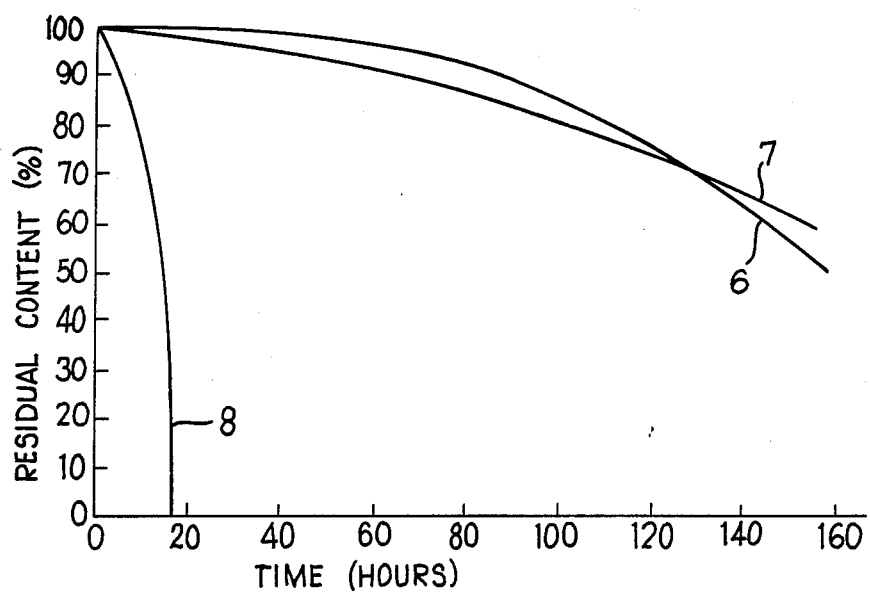
FIG. 3 is a graph showing the thermal stability of vitamin A powders of Example 6 and Comparative Example 6.

1 kg of activated gluten powder was added to 5 liters of hydrous ethanol having a content of the alcohol of 70 vol % and agitated for 30 minutes by means of an agitator. Thereafter, the mixture was centrifugally separated for 20 minutes at 3000 r.p.m. to separate crude glutenin (insoluble matters) from a supernatant liquid (hydrous alcohol dissolving gliadin). The supernatant liquid was concentrated to a gliadin concentration of 20% (w/v percent). On the other hand, the crude glutenin was washed three times with 70 vol % hydrous ethanol, after which 70 vol % hydrous ethanol was added so that a concentration of the solid matters was 20% (w/v percent). Vitamin A acetate (1,700,000 IU/g) was added to each of the two hydrous ethanol solutions in an amount of 20% (w/v percent) calculated as the solid matter, followed by agitation with a homomixer for 10 minutes, drying by means of a vacuum dryer, powdering and screening to obtain a powder with a size not larger than 50-mesh as a sample. The sample was subjected to a thermal stability test under the same conditions as in Example 1. It will be note that in FIG. 3, the vitamin A powder (6) indicates a vitamin A powder obtained using hydrous ethanol dissolving gliadin therein and the vitamin A powder (7) is a vitamin A powder obtained using the crude glutenin.

On the other hand, for comparison, an emulsion (using 2 wt % of an emulsifier) which was obtained by emulsifying vitamin A similar to one used above by means of an emulsifier (glycerine fatty acid ester) to have the same concentration as set out above was powdered in the same manner as described, thereby obtaining vitamin A powder (8). The results of the thermal stability test of this powder are also shown.

Example 7, Comparative Example 7

80 g of the activated gluten powder as used in Example 6 was added to 400 multiliters of hydrous ethanol containing 70 vol % of ethanol and agitated for 10 minutes by means of a high speed homomixer, followed by addition of 20 g of vitamin A palmitate (1,700,000 IU/g) under agitation, further agitation for 15 minutes and powdering the same manner as in Example 6 (vitamin A powder (9)).

On the other hand, vitamin A palmitate was added at such a concentration as used above to the hydrous ethanol solution dissolving gliadin and obtained in the same manner as in Example 6 and also to the hydrous ethanol to which the crude glutenin had been added, followed by repeating the procedure described above to obtain vitamin A powders (vitamin A powder (10) obtained by the use of gliadin and vitamin A powder (11) obtained by the use of the crude glutenin).

Figure 4:
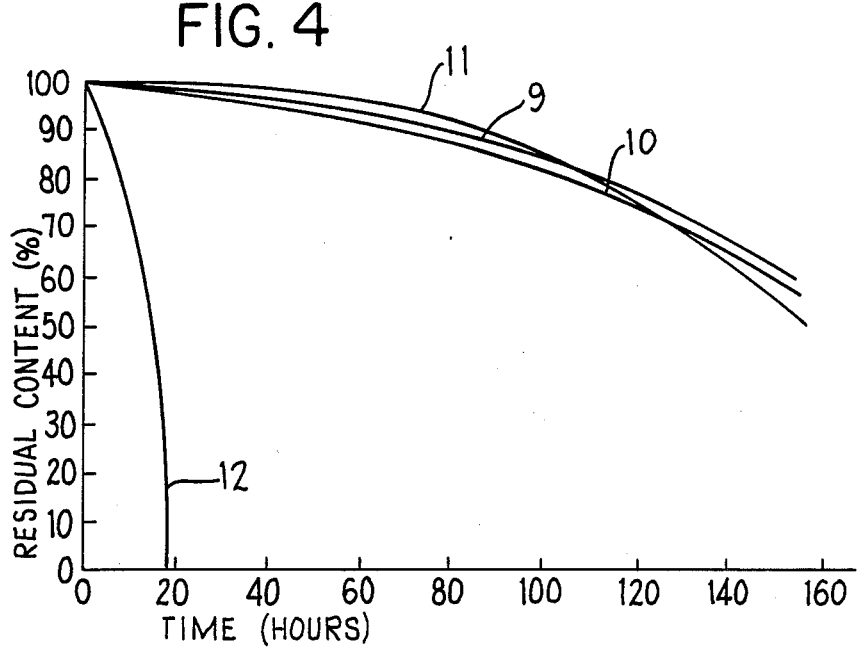
FIG. 4 is a graph showing the thermal stability of vitamin A powders of Example 7 and Comparative Example 7.

For comparison, an emulsion which was controlled to have a concentration of vitamin A as set forth above and was emulsified by the use of an emulsifier (glycerine fatty acid ester), dextrin and casein (with concentrations of the emulsifier, dextrin and casin of 2 wt %, 16.8 wt % and 11.2 wt %, respectively) was similarly powdered (vitamin A powder (12)). These vitamin A powders were screened to collect powders with a size not larger than 50 mesh and subjected to the thermal stability test under the same conditions as in Example 1. The results are shown in FIG. 4.

I claim:

1. A process for preparing a powder consisting essentially of an inclusion complex of at least one vitamin and gliadin, wherein said complex contains from 1 to 51 parts by weight of vitamin per 100 parts by weight of gliadin, which consists essentially of the steps of adding said vitamin to a solution consisting essentially of gliadin dissolved in a solvent capable of dissolving gliadin, mixing said vitamin with said solution, then removing said solvent to obtain the inclusion complex and then treating the inclusion complex to form same into a powder.

2. A process as claimed in claim 1 in which said solvent is selected from the group consisting of hydrous alcohols, dilute acids and dilute alkaline solutions.

3. A process as claimed in claim 1 in which said solvent is a hydrous alcohol composition containing from 20 to 80% by volume of an alcohol and the balance is water, said alcohol being selected from the group consisting of methyl alcohol, ethyl alcohol and isopropyl alcohol.

4. A process as claimed in claim 1 in which said solvent is hydrous ethanol containing from 65 to 75% by volume of ethanol.

5. A process as claimed in claim 1 in which said vitamin is mixed with said solution for from 10 to 45 minutes.

6. A process as claimed in claim 1 in which said vitamin is dissolved or dispersed in an animal or plant, oil or fat.

7. A process for preparing a powder composed of at least one vitamin and gliadin, which comprises the steps of adding said vitamin to a solution consisting essentially of gliadin dissolved in a solvent capable of dissolving gliadin, mixing said vitamin with said solution, then removing said solvent and then treating the residue to convert same to a powder.

* * * * *